(12) United States Patent
Drew et al.

(10) Patent No.: US 8,287,520 B2
(45) Date of Patent: Oct. 16, 2012

(54) AUTOMATED INTEGRITY TESTS

(75) Inventors: Touby A. Drew, Golden Valley, MN (US); Steven M. Goetz, North Oaks, MN (US)

(73) Assignee: Medtronic, Inc., Minneapolis, MN (US)

( * ) Notice: Subject to any disclaimer, the term of this patent is extended or adjusted under 35 U.S.C. 154(b) by 571 days.

(21) Appl. No.: 12/100,750

(22) Filed: Apr. 10, 2008

(65) Prior Publication Data
US 2009/0259216 A1 Oct. 15, 2009

(51) Int. Cl.
*A61K 9/22* (2006.01)
(52) U.S. Cl. ....... 604/891.1; 604/65; 604/131; 604/500; 607/27; 600/553
(58) Field of Classification Search ........... 604/8–10, 604/65–67, 131, 151, 500, 503, 890.1, 891.1, 604/48, 93.01; 607/27, 28, 29; 600/553
See application file for complete search history.

(56) References Cited

U.S. PATENT DOCUMENTS

| | | | |
|---|---|---|---|
| 4,545,380 A | 10/1985 | Schroeppel | |
| 4,634,426 A * | 1/1987 | Kamen | 604/65 |
| 4,825,869 A | 5/1989 | Sasmor et al. | |
| 5,003,975 A | 4/1991 | Hafelfinger et al. | |
| 5,201,865 A | 4/1993 | Kuehn | |
| 5,507,786 A | 4/1996 | Morgan et al. | |
| 5,607,455 A | 3/1997 | Armstrong | |
| 5,620,475 A * | 4/1997 | Magnusson | 607/30 |
| 5,660,183 A | 8/1997 | Chiang et al. | |
| 5,891,179 A | 4/1999 | Er et al. | |
| 5,925,066 A * | 7/1999 | Kroll et al. | 607/3 |
| 6,021,352 A * | 2/2000 | Christopherson et al. | 607/42 |
| 6,317,633 B1 | 11/2001 | Jorgenson et al. | |
| 6,387,048 B1 | 5/2002 | Schulman et al. | |
| 6,475,180 B2 | 11/2002 | Peterson et al. | |
| 6,497,655 B1 | 12/2002 | Linberg et al. | |
| 6,721,600 B2 | 4/2004 | Jorgenson et al. | |
| 6,804,558 B2 | 10/2004 | Haller et al. | |

(Continued)

FOREIGN PATENT DOCUMENTS

EP 1 493 460 A1 1/2005

(Continued)

OTHER PUBLICATIONS

U.S. Appl. No. 11/414,786, filed Apr. 28, 2006, entitled: "Automatic Lead Functionality Testing," by Goetz et al.

(Continued)

*Primary Examiner* — Kevin C Sirmons
*Assistant Examiner* — Kami A Bosworth
(74) *Attorney, Agent, or Firm* — Shumaker & Sieffert, PA (57) ABSTRACT

Techniques for testing integrity of various elements of implantable medical device systems are described. Some embodiments automatically test the integrity of one or more system elements in response to detecting an event. Examples of events in response to which an integrity test may be performed include the patient being within a target activity state, a symptomatic event experienced by a patient, an external impact on the patient that exceeds a damage threshold, or an indication that the patient is receiving inappropriate therapy. Some embodiments automatically test integrity in response to failure to autonomously detect an event, which may be indicated by input from a patient. An implantable lead carrying electrodes or a therapeutic substance delivery element, such as a catheter, are examples of system elements for which integrity may be tested in some embodiments.

43 Claims, 6 Drawing Sheets

U.S. PATENT DOCUMENTS

| | | |
|---|---|---|
| 7,047,083 B2 | 5/2006 | Gunderson et al. |
| 2002/0087115 A1 | 7/2002 | Hartlaub |
| 2002/0095196 A1 | 7/2002 | Linberg |
| 2002/0120307 A1 | 8/2002 | Jorgenson et al. |
| 2004/0064161 A1 | 4/2004 | Gunderson et al. |
| 2004/0138516 A1* | 7/2004 | Osorio et al. ............ 600/9 |
| 2004/0138711 A1 | 7/2004 | Osorio et al. |
| 2004/0162593 A1 | 8/2004 | Jorgenson et al. |
| 2005/0080460 A1 | 4/2005 | Wang et al. |
| 2005/0096708 A1 | 5/2005 | Seim et al. |
| 2005/0215947 A1* | 9/2005 | Heruth et al. ............ 604/66 |
| 2005/0245988 A1* | 11/2005 | Miesel ............ 607/46 |
| 2006/0017576 A1 | 1/2006 | Gordon et al. |
| 2006/0107148 A1 | 5/2006 | Ginggen et al. |
| 2006/0111659 A1 | 5/2006 | Tyler |
| 2006/0122652 A1 | 6/2006 | Das |
| 2006/0122863 A1 | 6/2006 | Gottesman et al. |
| 2007/0018809 A1* | 1/2007 | Reiter et al. ............ 340/539.11 |
| 2007/0293903 A1 | 12/2007 | Bohn et al. |
| 2009/0138061 A1* | 5/2009 | Stephens et al. ............ 607/41 |

FOREIGN PATENT DOCUMENTS

| | | |
|---|---|---|
| WO | WO 2008/039242 A1 | 4/2008 |

OTHER PUBLICATIONS

U.S. Appl. No. 11/414,536, filed Apr. 28, 2006, entitled: "Distributed Lead Functionality Testing," by Goetz et al.

U.S. Appl. No. 11/413,072, filed Apr. 27, 2006, entitled: "Event-Based Lead Impedance Monitoring," by Touby A. Drew.

Notification of Transmittal of the International Search Report and the Written Opinion of the International Searching Authority, or the Declaration dated Jul. 16, 2009 for Application No. PCT/US2009/030915 (11 pgs.).

* cited by examiner

AUTOMATED INTEGRITY TESTS

TECHNICAL FIELD

The invention relates to implantable medical devices, and more particularly to testing the integrity of implantable medical devices.

BACKGROUND

Implantable medical devices are used for a variety of applications, which may include one or both of patient sensing and therapy delivery. For example, implantable medical devices are used to deliver therapy to patients to treat a variety of symptoms or conditions such as chronic pain, tremor, Parkinson's disease, multiple sclerosis, spinal cord injury, cerebral palsy, amyotrophic lateral sclerosis, dystonia, torticollis, epilepsy, pelvic floor disorders, gastroparesis, cardiac arrhythmia, or obesity. Some implantable medical devices deliver electrical stimulation in the form of electrical pulses or substantially continuous signals, via one or more leads that include electrodes located proximate to a target therapy delivery site. Some implantable medical devices chronically deliver metered dosages of a therapeutic agent, such as pharmaceutical agents, insulin, pain relieving agents, gene therapy agents, or the like, to a target therapy delivery site via a catheter. The target therapy delivery site may be, for example, a nerve or other tissue site, such as a spinal cord, pelvic nerve, pudendal nerve, stomach, bladder, or within a brain or other organ of a patient, or within a muscle or muscle group of a patient. In some embodiments, multiple therapy types, e.g., electrical stimulation and therapeutic agent delivery, may be used simultaneously to deliver optimal and efficient therapy to a patient.

Some implantable medical devices are used for patient sensing or monitoring alone, while others provide sensing in addition to therapy. Some implantable medical devices deliver therapy based on or in response to one or more sensed physiological parameters of a patient. Examples of physiological parameters that may be monitored include activity level or movement, posture, pressure, temperature, the concentration of one or more substances within the patient such as glucose, electrical activity of the brain such as an encephalogram (EEG), electrical activity of the heart such as an electrocardiogram (ECG), or muscle activity such as an electromyogram (EMG). Sensors used to detect physiological parameters include accelerometers, thermistors, capacitive sensor, optical sensors and electrodes, which in some cases may also be used for delivery of electrical stimulation.

In order for an implantable medical device to continue to provide effective therapy and/or monitoring, each of the elements or components of the implantable medical device, or a system including the implantable medical device, must continue to operate as expected. In some cases, in order to ensure or verify effective operation, integrity tests are performed on various elements of an implantable medical device system. For example, lead integrity tests have been performed on implantable leads carrying electrodes for delivery of electrical stimulation and sensing by an implantable medical device.

Typically, such integrity tests have been performed manually, by a clinician, during a follow-up visit with the patient. However, integrity tests performed only at follow-up visits may detect a component failure too late, or fail to detect an intermittent problem, such as an intermittent lead fracture. This may leave the patient without appropriate therapy or sensing for a period of time away from the clinic.

It has also been proposed to automatically perform integrity tests at regular, periodic intervals, e.g., once per day, when the patient is away from the clinic. However, regular integrity tests consume a significant amount of power from a power source of the implantable medical device. Furthermore, such regular integrity tests may still fail to detect an intermittent problem which does not manifest during the test.

SUMMARY

In general, the invention is directed toward techniques for testing integrity of various elements of implantable medical device systems. Some embodiments automatically test the integrity of one or more system elements in response to detecting an event. Some embodiments automatically test integrity in response to failure to autonomously detect an event. The failure to autonomously detect an event may be indicated by input from a patient. By automatically performing an integrity test based on detection or failure to detect an event, problems with elements of an implantable medical device system may be detected away from the clinic. Furthermore, by automatically performing an integrity test based on detection or failure to detect an event, the test may be more likely to detect an intermittent failure without consuming as much power as may be required for regular, periodic testing.

An implantable lead carrying electrodes or a therapeutic substance delivery element, such as a catheter, are examples of system elements for which integrity may be tested in some embodiments. Other examples include sensors, other hardware elements, and firmware or other software elements. In some embodiments, an event detected via a first sensor that detects a first physiological parameter of a patient is used as a basis to test integrity of one or more other sensors that detect other physiological parameters of the patient. For example, the first sensor may indicate that the patient is not receiving appropriate therapy, in response to which some embodiments may test another sensor used for controlling delivery of therapy, as well as therapy delivery elements (e.g., leads or catheters), or other system elements.

An example of an event in response to which an integrity test may be performed is the patient being within a target activity state. For example, intermittent kinking or occlusion of a catheter may be more likely to manifest when a patient is very active. Another example event is a symptomatic event experienced by a patient, which may not actually be a symptomatic event, but may instead indicate a problem with a system element. Other examples are a force experienced by or applied to the patient with a magnitude that exceeds a damage threshold, or, as discussed above, an indication that the patient is receiving inappropriate therapy.

In one embodiment, the invention is directed toward a method comprising monitoring a signal from a sensor that detects a physiological parameter of a patient, determining whether an event is detected based on the signal, and automatically testing integrity of a therapeutic substance delivery element based on the determination of whether the event is detected. The therapeutic substance delivery element delivers a therapeutic substance from an implantable medical device to a target therapy delivery site in the patient In another embodiment, the invention is directed toward an implantable medical device comprising an integrity measurement module configured to test integrity of a therapeutic substance delivery element that delivers a therapeutic substance from the implantable medical device to a target therapy delivery site in a patient, and a processor. The processor monitors a signal from a sensor that detects a physiological parameter of the patient, determines whether an event is detected based on the signal, and automatically controls the integrity measurement module to test integrity of the therapeutic substance delivery element based on the determination.

In yet another embodiment, the invention is directed toward a method comprising monitoring a first signal from a first sensor of an implantable medical device system, wherein the first sensor detects a first physiological parameter of a patient, determining that the patient is not receiving appropriate therapy based on the first signal, and automatically testing integrity of at least one other element of the implantable medical device system based on the determination. The at least one other element comprises at least one of a therapy delivery element, a second sensor that detects a second physiological parameter of the patient, a software element, a firmware element, or a hardware element.

In yet another embodiment, the invention is directed toward an implantable medical device comprising an integrity measurement module, and a processor that monitors a signal from a first sensor that detects a first physiological parameter of a patient, determines that a patient is not receiving adequate therapy based on the first signal, and automatically controls the integrity measurement module to test integrity of at least one other element of an implantable medical device system that includes the implantable medical device based on the determination. The at least one other element comprises at least one of a therapy delivery element, a second sensor that detects a second physiological parameter of the patient, a software element, a firmware element, or a hardware element.

In yet another embodiment, the invention is directed toward a method comprising monitoring a signal from a sensor of an implantable medical device system that detects at least one of activity or posture of a patient, detecting an acceleration with a magnitude exceeding a threshold based on the signal, and automatically testing integrity of at least one element of the implantable medical device system in response to the detection. The at least one other element comprises at least one of a therapy delivery element, the sensor, another sensor that detects another physiological parameter of the patient, a software element, a firmware element, or a hardware element.

In yet another embodiment, the invention is directed toward an implantable medical device comprising an integrity measurement module, and a processor that monitors a signal from a sensor that detects at least one of activity or posture, detects an acceleration with a magnitude exceeding a threshold based on the signal, and automatically tests integrity of at least one element of the implantable medical device system in response to the detection. The at least one other element comprises at least one of a therapy delivery element, the sensor, another sensor that detects another physiological parameter of the patient, a software element, a firmware element, or a hardware element.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
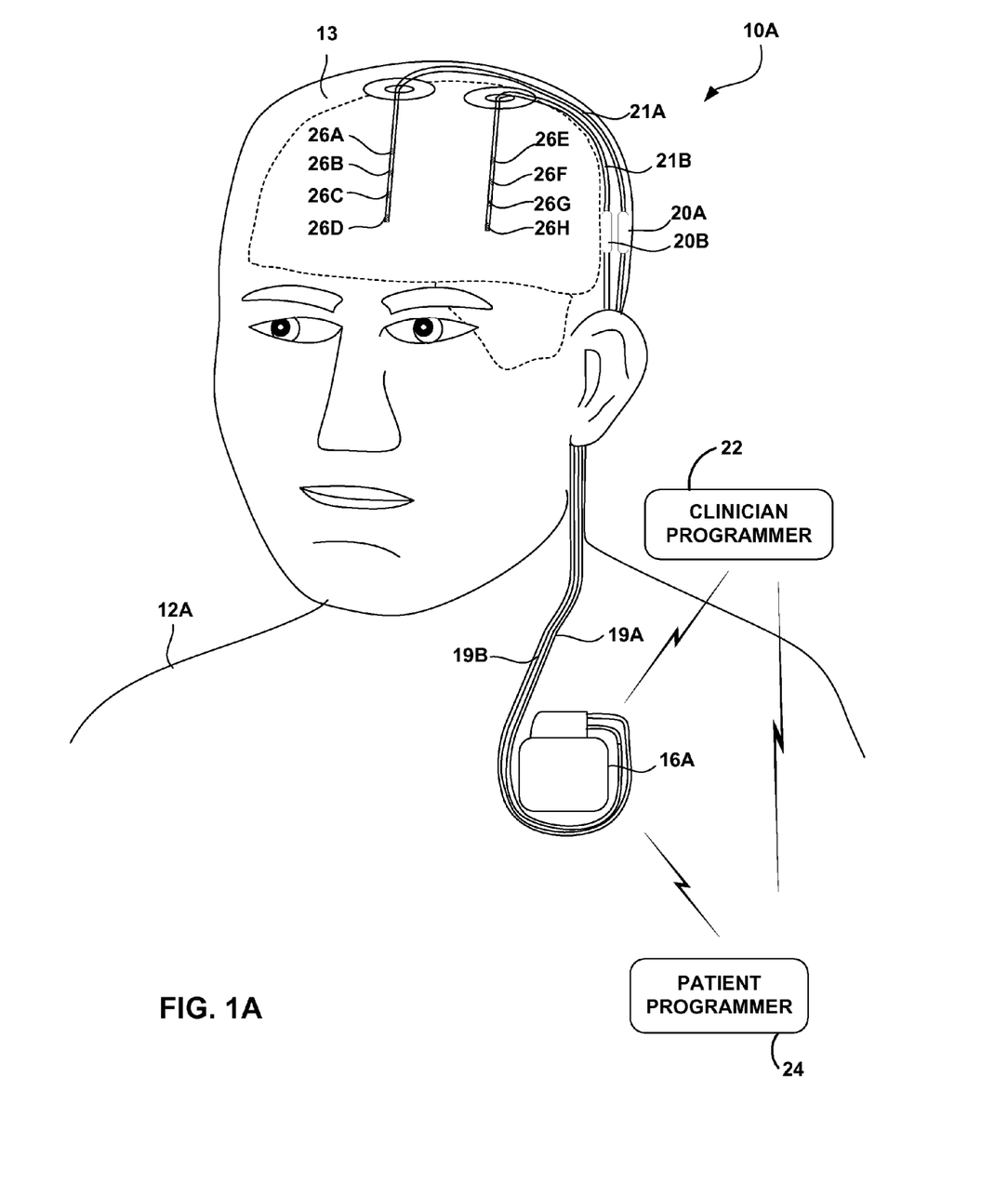
FIGS. 1A and 1B are conceptual diagrams illustrating example systems that include example implantable medical devices that perform automatic integrity tests.
Figure 1B:
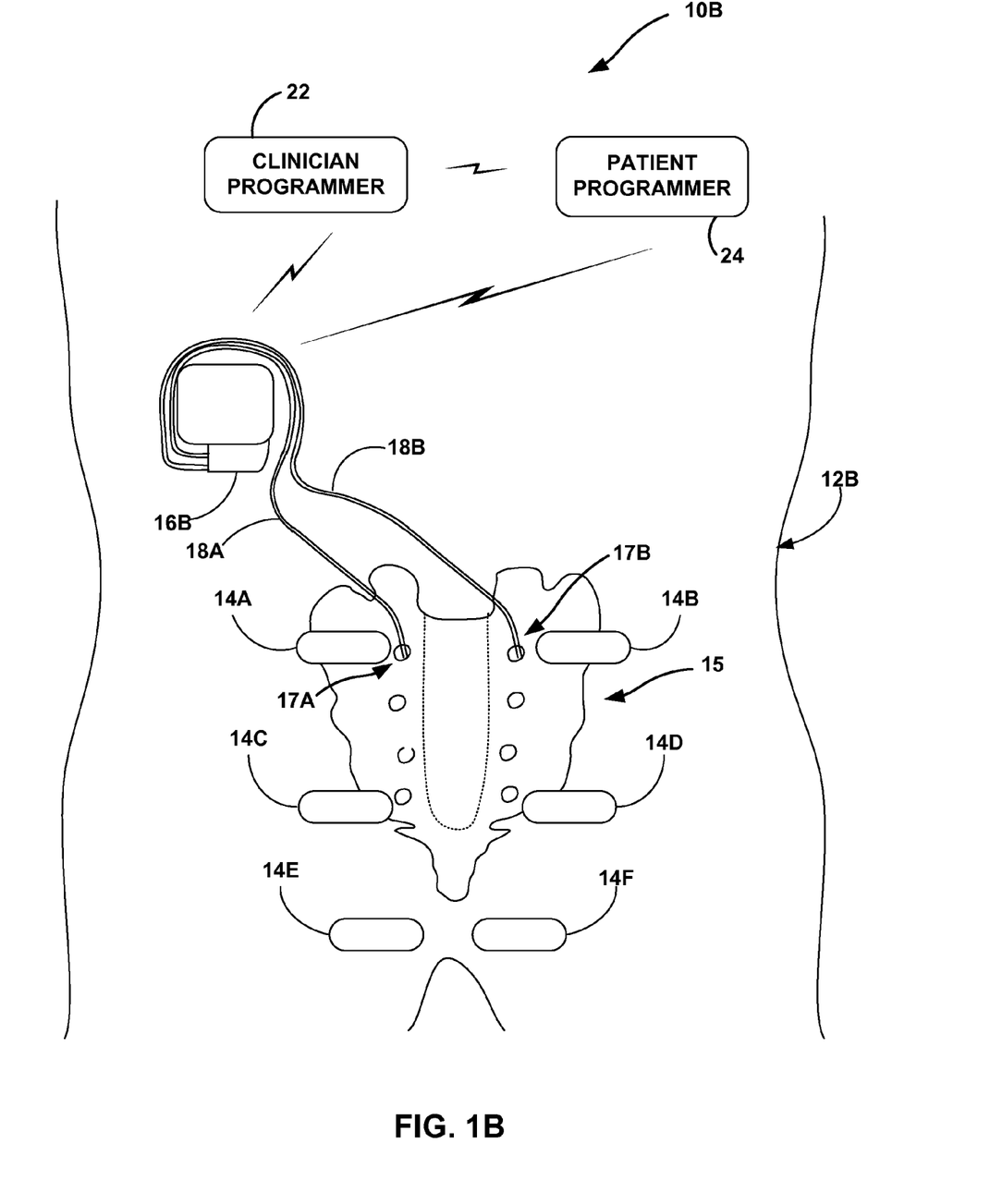

FIGS. 1A and 1B are conceptual diagrams illustrating example systems 10A and 10B (collectively "systems 10") that include example implantable medical devices (IMDs) 16A and 16B (collectively "IMDs 16) that perform automatic integrity tests in accordance with the present invention. In the example illustrated by FIG. 1A, IMD 16A is coupled to a leads 21A and 21B (collectively "leads 21") by respective lead extensions 19A and 19B (collectively "lead extensions 19"). Lead extensions 19 and leads 21 are coupled by respective connectors 20A and 20B (collectively "connectors 20"). Leads 21 include a plurality of electrodes 26A-26H (collectively "electrodes 26") at their distal ends, which are implanted within the brain 13 of a patient 12. In some embodiments, a leads 2, as well as any associated extension 19 and connector 20, may collectively be referred to as an "implantable medical lead."

The number and position of electrodes 26, leads 21, lead connectors 20 and extensions 19 illustrated in FIG. 1A are exemplary. For example, system 10A may include any one or more leads 21, each including one or more electrodes 26, and need not include any extensions 19 or connectors 20. Leads 21 may be a substantially cylindrical, percutaneously implantable leads, and electrodes 26 may be ring electrodes.

However, in other embodiments, leads 21 may have other shapes, such as paddle-like shapes with electrodes located on one or more sides of the paddle, or may include a complex, multi-dimensional electrode array geometry. For example, leads 21 may have a substantially cylindrical shape, and include a plurality of non-ring electrodes located at various circumferential and axial positions thereon. As another example, a distal end of one of leads 21 may include a "cuff-like" element, with one or more leads disposed about the interior of the cuff. Further, in addition to or as an alternative to electrodes 26 located on leads 21, one or more electrodes with associated electrical paths may be located on or near, or provided by, the housing or header of IMD 16A.

IMD 16A may sense electrical activity via electrodes 26. In some embodiments, IMD 16A also delivers stimulation via electrodes 26. IMD 16A may deliver stimulation based on or in response to the sensed electrical activity, e.g., to provide a closed-loop therapy. For example, in response to detecting a seizure, IMD 16A may deliver electrical stimulation to target tissues, such as the hippocampus, anterior nucleus of the thalamus, temporal lobe, or other regions in brain 13, via a plurality of electrodes 26 to terminate the seizure.

The invention is not limited to implementation by IMDs that detect and treat seizures, or even embodiments in which leads 21 are located within brain 13. An IMD 16 according to the invention may provide sensing and/or treatment for any neurological, gastrological, urological, muscular, or cardiac symptom or malady. In some embodiments, an IMD 16 may be coupled to electrodes 26 implanted near or within the spinal cord, heart, stomach, intestines, colon, or bladder, or within muscle or the pelvic floor of patient 12. An IMD 16 may sense an EEG, ECG, EMG, or other electrical signals within patient 12 via electrodes 26, and may deliver electrical stimulation to, for example, treat pain, provide functional electrical stimulation, prevent arrhythmias, or prevent incontinence. The invention is not limited to neurostimulators, and is further not limited to implantable medical devices that provide stimulation.

FIG. 1B is a conceptual diagram illustrating another example implantable medical device system 10B, which includes IMD 16B coupled to therapeutic substance delivery elements 18A and 18B, which will be referred to as catheters 18A and 18B (collectively "catheters 18") throughout this disclosure. IMD 16B provides one or more therapeutic agents that are delivered to target therapy delivery sites 17A and 17B (collectively "target therapy delivery sites 17") by catheters 18A and 18B, respectively. In the example of FIG. 1, IMD 16B is implanted in patient 12 proximate to target therapy delivery sites 17. However, in other embodiments, IMD 16B may be implanted at another location in the body of a patient 12 (e.g., in a chest cavity, lower back, lower abdomen, or buttocks of patient 12). In the illustrated embodiment, IMD 16B is coupled to two catheters 18 to deliver therapy to two target therapy delivery sites 17. In other embodiments, IMD 16 may be coupled to a single catheter or more than two catheters, e.g., to deliver therapy to more or fewer target therapy delivery sites.

In the embodiment of therapy system 10B shown in FIG. 1, target therapy delivery sites 17 are proximate to the sacrum 15, and catheters 18 have been introduced into the sacral foramens 17A and 17B of sacrum 15. Accordingly, catheters 18 may deliver therapy to, for example, the sacral or pudendal nerves or surrounding tissue. Therapeutic agent delivery to the sacral nerves, pudendal nerves or surrounding tissue may help treat pelvic floor disorders, urinary control disorders, fecal control disorders, interstitial cystitis, sexual dysfunction, or pelvic pain, as examples. Therapy system 10B, however, may be applied to deliver a variety of therapies formulated for different disorders or symptoms, such as chronic pain, tremor, Parkinson's disease, multiple sclerosis, spinal cord injury, cerebral palsy, amyotrophic lateral sclerosis, dystonia, torticollis, epilepsy, pelvic floor disorders, gastroparesis, or obesity. Thus, in alternate embodiments, target therapy delivery sites 17 may be proximate to any other nerve or tissue site in body 12, which may be selected based on, for example, a therapy program selected for a particular patient. For example, target therapy delivery sites 17 may be proximate to a spinal cord, pelvic nerve, pudendal nerve, stomach, bladder, or within a brain, intrathecal space, or other cavity or organ of patient 12, or within a muscle or muscle group of patient 12.

As further shown in FIG. 1B, system 10B may include one or more distributed sensing devices 14A-14F (collectively "sensing devices 14" or "sensors 14"). Sensors 14 may detect one or more physiological parameters of patient 12, such as activity, posture, pressure, concentration of a chemical or other substance, temperature, and/or an electrical signal, such as an EEG, ECG, or EMG. Sensors 14 may comprise, as examples, electrodes, such as electrodes 26 (FIG. 1A), an accelerometer, a piezoelectric element, a pressure sensitive capacitor, an optical sensor, or a thermistor. Sensors 14 may generate signals based on the detected physiological parameter, and communicate such signals to IMD 16 via leads (not shown), conductors within catheters 18, or wireless telemetry. Additionally or alternatively, one or more sensors 14 may be located on or within IMD 16B and/or externally coupled to patient 12.

The physiological parameters sensed by sensors 14 may be useful in identifying a state or phase of physiological activity, or a transition between different phases of activity. IMD 16B may use information received from sensors 14 to adjust or initiate therapy delivery. For example, IMD 16B may use information received from sensors 14 to adjust therapy parameters such as dosage, pulse rate, pump stroke, or any other therapy parameters, or to initiate a bolus of the therapeutic agent. IMD 16B may adjust therapy delivery based on other information, such as user input or timing information, either individually or in combination with information received from sensors 14. Although not illustrated in FIG. 1A, IMD 16A may similarly be coupled to or include one or more sensors 14. In some embodiments, as discussed above, electrodes 26 may act as sensors 14.

IMDs 16 (FIGS. 1A and 1B) may monitor signals from one or more of sensors 14, determine whether an event is detected based on the signal, and automatically perform an integrity test, e.g., make an integrity measurement, based on the determination. For example, a sensor that detects at least one of activity, posture, or pressure, such as an accelerometer, piezoelectric sensor, or pressure sensitive capacitor, may detect an external impact or some other external force experienced by or applied to patient 12. Embodiments may determine whether a magnitude of the force exceeds a threshold. The sensor used in this detection will primarily be referred to below as an activity sensor, although the sensor is not limited to detecting activity and may detect activity, posture, pressure, or any combination thereof, in various embodiments.

Examples of external forces that the activity sensor may detect include an apparent patient fall, collision, deceleration associated with an automobile or other accident, or any other event that may cause damage to one or more elements of therapy delivery system 10. In some embodiments, the external impact or other force may cause a sharp change in the signal sensed by the activity sensor. The sensor may detect, but is not limited to detecting, external impacts. The sensor may detect any acceleration or force with a magnitude that exceeds the threshold. Additionally, a force, e.g., acceleration, exceeding the threshold may be detected irrespective of the direction of the force, e.g., acceleration, relative to the patient or the sensor within or on the patient. For example, the detection may be based on the magnitude, e.g., absolute value, of the signal generated by the sensor as a function of the external force.

A detected impact or other force that exceeds the threshold may cause damage to therapy system 10. In such cases, the threshold may be a system damage threshold. The system damage threshold may be set at a level corresponding to or below what is anticipated as possibly damaging system 10. In this manner, not all detected impacts or other external forces that exceed the threshold will necessarily result in damage to system 10. In some embodiments, the threshold is set a margin or factor of safety below a force magnitude that would likely damage system 10.

Furthermore, some embodiments may detect impacts or other external forces for other reasons instead of, or in addition to, detecting events that could result in system damage. For example, in some cases, a detected impact or other force may be the result of inappropriate functioning of therapy system 10, e.g., when inappropriate therapy causes patient 12 to collapse, which collapse may or may not be sufficient to damage system 10. In such cases, embodiments may perform one or more integrity checks in response to the detection of a force exceeding the threshold to identify possible causes of impact or other external force, e.g., possible causes of the inappropriate therapy leading to the impact or other external force.

If the detected force exceeds the threshold, IMD 16 may automatically perform an integrity measurement. Automatically performing an integrity measurement in response to a detected acceleration may aid to detecting problems with therapy system 10 that may result from such an acceleration. Automatically performing an integrity measurement in response to a detected acceleration may also aid in detecting problems with therapy system 10 that may be causing patient 12 to receive inappropriate therapy.

In another embodiment, detecting an event may comprise detecting an abnormality in a signal from a sensor (e.g., one of sensors 14). The abnormality may be a value outside of an expected physiological range, abnormal energy content in a particular frequency band, a quiescent (e.g., substantially flat) signal segment, saturation, or a high slew rate, which may demonstrate signal railing. As one example, an electroencephalogram (EEG) signal sensed by a sensing device may include relatively low energy content in a particular frequency band that may indicate that patient 12 is not alert, possibly as a result of receiving inadequate therapy.

Abnormal measurements from a sensor may reflect damage to the sensor producing the abnormal signal. Abnormal measurements from a sensor may alternatively indicate that the patient is not receiving appropriate therapy due to damage to another sensor used for controlling the therapy, damage to the therapy delivery system (e.g., damage to IMD 16, leads 21, or catheters 18), or an internal software, firmware, or hardware issue. For example, overdose or underdose due to an inappropriate sensor measurement or inappropriate therapy delivery may be reflected in detectable changes in a patient's physiological state.

In response to detecting an abnormal signal from a sensor, IMD 16 may determine that patient 12 is not receiving adequate therapy. For example, IMD 16 may test the sensor that is producing the abnormal signal to determine if the abnormal reading is due to patient 12 not receiving adequate therapy rather than that particular sensor being dysfunctional. As another example, IMD 16 may analyze the signals from multiple sensors to determine if the abnormal reading is the result of a dysfunctional sensor or inadequate therapy delivery. If patient 12 is not receiving adequate therapy, it may be reflected in more than one sensor. If IMD 16 determines that patient 12 is not receiving adequate therapy, IMD 16 may automatically perform an integrity measurement.

In other embodiments, an event may comprise a symptomatic event, such as occurrence of a symptom that therapy delivery system 10 is intended to treat. For example, in one embodiment, a symptomatic event may be a seizure. However, the invention is not so limited, and a symptomatic event may alternatively be any neurological, gastrological, urological, muscular, or cardiac symptomatic event detectable via therapy delivery system 10. Symptomatic events are described in further detail in copending U.S. patent application Ser. No. 11/413,072 by Touby A. Drew, entitled, "EVENT-BASED LEAD IMPEDANCE MONITORING," which is incorporated herein by reference in its entirety.

In yet other embodiments, an event may comprise determining that patient 12 is in a target activity state, as described in copending U.S. patent application Ser. No. 11/414,786 by Steven M. Goetz et al., entitled, "AUTOMATIC LEAD FUNCTIONALITY TESTING," which is incorporated herein by reference in its entirety. In some embodiments, IMD 16 determines whether patient 12 is in a target activity state based on an activity and/or physiological sensor signal, e.g., one or more accelerometer signals. In such embodiments, IMD 16 automatically performs an integrity measurement when patient 12 is in the target activity state. A target activity state may be one in which integrity testing will be unobtrusive. For example, in embodiments in which therapy delivery is suspended when integrity measurements are taken, the target activity state may occur when the absence of therapy will likely not be noticed, such as when patient 12 is asleep. Additionally or alternatively, a target activity state may be one during which an integrity measurement is more likely to capture information of particular interest. For example, IMD 16 may perform an integrity measurement when patient 12 is in a particular posture, or changing postures or otherwise active, which may allow the medical device to identify intermittent problems with therapy delivery system 10 that may occur when patient 12 is in a target activity state (e.g., kinking in catheters 18 when patient 12 is in a particular position).

An integrity measurement may be automatically performed in response to detecting an event. An integrity measurement may generally comprise a measurement that tests the functionality of any component of therapy system 10. For example, performing an integrity measurement may comprise running software, hardware, and/or firmware diagnostics to test the integrity of IMD 16.

As a further example, with respect to system 10B of FIG. 1B, IMD 16B may perform a pressure measurement in one or more of catheters 18 as an integrity measurement. For example, IMD 16B may measure a pressure within one or more of catheters 18 for comparison to a pressure within a pump of IMD 16B or an expected, normal pressure value. Such a measurement may aid to detecting flow issues within the catheter. If functioning properly, the pressure within catheters 18 may be substantially constant. Thus, for a given flow rate the pressure within a catheter may be approximately equal to a normal, expected level. Deviations from the normal pressure may indicate failure of the catheter. A pressure measurement below the normal level may indicate that the catheter is ripped or leaking. A pressure measurement above the normal level may indicate that the catheter is occluded or kinked. In other embodiments, the flow of a therapeutic substance within one or more of catheters 18 may be measured to identify issues (e.g., occlusions, kinks, tears, and leaks) with catheters 18.

In embodiments in which IMD 16B comprises a pump that delivers a therapeutic substance from IMD 16B to target therapy delivery sites 17, performing an integrity measurement may comprise changing an operating parameter of the pump and monitoring how therapy system 10 is affected. For example, a pumping characteristic that differs substantially from the pumping characteristic used to deliver therapy may be used to aid in determining if therapy system 10 is functioning properly and, if applicable, what is causing therapy system 10 to function improperly.

In one embodiment of performing an integrity measurement, the modified pumping characteristic comprises a modified pump stroke. The pump stroke may be increased and the pulses may be distributed to maintain a similar average flow rate of therapeutic substance to patient 12. The way that the pulses are delivered to patient 12 can be used to determine what is wrong with therapy delivery system 10B and may potentially help address the issue. For example, if one of catheters 18 is partially occluded, a higher pulse stroke may aid in clearing the occlusion from catheter 18. In another embodiment, the integrity of the pump may be tested by driving the pump backwards (e.g., firing against the piston of the pump motor). This type of integrity measurement may be used to determine if a problem with therapy delivery system 10B is due to a moving part within the pump or an issue with one or more of catheters 18. The pump may comprise a piston-based pump, rotary pump, or any type of pump known in the art.

As yet a further example, with respect to system 10A of FIG. 1A, IMD 16A may perform an integrity measurement that comprises an impedance measurement as described in copending U.S. patent application Ser. No. 11/413,072 by Touby A. Drew, entitled, "EVENT-BASED LEAD IMPEDANCE MONITORING." For example, IMD 16A may perform an implantable medical lead integrity test by measuring the impedance of one or more "electrical paths," which may include one of electrodes 26, the conductors and contacts within lead 21, connector 20 and extension 19 associated with the electrode, and tissue proximate to the electrode. Accordingly, because lead 21 includes four electrodes 26, the lead may include four electrical paths. In other embodiments, however, an electrical path may include a plurality of electrodes 26 coupled to IMD 16A. Measuring the impedance of one or more electrical paths associated with one or more leads 21 coupled to the medical device may aid in identifying dysfunctional electrical paths (e.g., paths that may be unable to provide adequate or reliable sensing or therapy due to, for example, degradation of the lead material, tissue growth proximate to an electrode, a short, or a fracture) among the paths provided by one or more leads coupled to a medical device.

As yet another example, an integrity measurement may comprise a sensor confirmation test. A sensor confirmation test may be performed on a sensor whose output can be influenced in a known manner when patient 12 performs a set of tasks. For example, implant system 10 may prompt patient 12 to assume one or more postures or activities, and system 10 may verify that the postures/activities are observed. If system 10 fails to observe a task that patient 12 performs during the sensor confirmation test, an integrity issue with the sensor is detected.

In some embodiments, a certain type of integrity measurement may be taken based on the type of event detected. For example, one embodiment of the invention may comprise determining whether an event is detected based on a signal from a sensor 14 that detects a physiological parameter of patient 12 and automatically checking integrity of a therapeutic substance delivery element (e.g., one or more of catheters 18) based on the determination. In another embodiment, IMD 16 may determine that patient 12 is not receiving adequate therapy based on a signal from a sensor (e.g., one of sensing devices 14) that detects at least one of an activity or physiological state of patient 12 and automatically checking integrity of at least one of a therapy delivery element (e.g., one or more of catheters 18 or leads 21), another sensor, a software element, a firmware element, or a hardware element based on the determination. In yet another embodiment of the invention, IMD 16 may detect an external force, e.g., acceleration, applied to or experienced by patient 12 based on a signal from a sensor (e.g., one of sensors 14), determine whether the force exceeds a threshold, and automatically check integrity of at least one of a therapy delivery element (e.g., one or more of catheters 18 or leads 21), the sensor, another sensor, a software element, a firmware element, or a hardware element based on the determination.

IMDs 16 may respond in a variety of ways to identification of a dysfunctional system component, including disabling the component. For example, IMDs 16 may modify sensing or therapy programs to not include a sensor, catheter, or electrical path with an identified integrity issue. Further, IMDs 16 may notify patient 12, a clinician, or some other entity, device, or system of the detection of an integrity problem with a system element.

As illustrated in FIGS. 1A and 1B, systems 10 may also include an external clinician programmer 22 and an external patient programmer 24 that transcutaneously communicate with IMDs 16A and 16B, such as via radio-frequency telemetry. Programmers 22 and 24 may be hand-held computing devices respectively associated with a clinician and patient 12. Clinician programmer 24 may be a more fully-featured device than patient programmer 24.

Clinician programmer 22 may be a handheld computing device that permits a clinician to program therapy for patient 12, e.g., using input keys and a display. For example, using clinician programmer 22, the clinician may specify values of therapy parameters for use in delivery of therapy. As examples, therapy parameters may include amplitude, pulse width, pulse rate or frequency, or a configuration of electrodes 26 (whether each electrode is a cathode, anode or off) in the case of electrical stimulation, or dosage, pulse rate, or pump stroke in the case of therapeutic substance delivery. Clinician programmer 22 supports telemetry (e.g., radio frequency telemetry) with IMD 16 to download therapy parameters and, optionally, upload operational or physiological data stored by IMDs 16. In this manner, the clinician may periodically interrogate IMDs 16 to evaluate efficacy and, if necessary, modify the therapy parameters.

Patient programmer 24 may also include a display and input keys to allow patient 12 to interact with patient programmer 24 and IMD 16. In this manner, patient programmer 28 provides patient 12 with an interface for control of therapy by IMD 16. For example, patient 12 may use patient programmer 24 to start, stop or adjust therapy. In particular, patient programmer 24 may permit patient 12 to adjust therapy parameters within an adjustment range specified by the clinician via clinician programmer 22, or select from a library of stored therapy programs.

IMDs 16 may alert patient 12 if an integrity issue with an element of systems 10 has been identified, e.g., via a vibratory, auditory, stimulatory or other alert. Further, in some embodiments, IMDs 16 may alert patient 12 via programmer 24, e.g., programmer 24 may provide an alert in response to receiving a signal from an IMD 16 that indicates an integrity issue with one or more elements of a system 10.

In some embodiments, IMDs 16 may provide more detailed information regarding the integrity issue to programmer 24, which the programmer may then provide to patient 12, e.g., via a display. Programmer 24 may also suggest a course of action based on such signals or information. For example, based on a signal from IMDs 16, programmer 24 may advise patient 12 that sensing or therapy may have been impaired or modified, or direct the patient to visit a clinician. As one example, when an IMD 16 identifies an intermittent integrity issue with an element of a system 10, an IMD 16 may provide patient 12 with information identifying one or more specific postures and/or activities that correlate with the integrity issue via programmer 24. In some embodiments, an IMD 16 may request that patient 12 avoid one or more specific postures and/or activities that correlate with the detected issue until patient 12 visits a clinician.

Similarly, based on more detailed information from IMDs 16, programmer 22 may advise the clinician of the one or more elements of system 10A with integrity issues, identify any actions automatically taken by an IMD 16 in response to the identification of the integrity issue, or advise the clinician to reconfigure or reprogram the IMD 16 in response to the integrity issue. For example, an IMD 16 or programmer 22 may instruct the clinician to avoid use of an electrical path with an identified integrity issue. In some cases, programmer 22 may advise the clinician to replace one or more of leads 21, connectors 24 and extensions 22, catheters 18, or IMD 16 itself, or to perform a software or firmware update. In embodiments in which IMD 16 automatically alters therapy to avoid use of one or more elements of a system 10 with integrity issues, IMD 16 may provide information about the therapy modification (e.g., when, why, and how the therapy modification occurred). IMD 16 may also advise a clinician of where data related to an integrity issue and/or therapy modification is stored.

An IMD 16, clinician programmer 22, and patient programmer 24 may communicate via cables or a wireless communication, as shown in FIG. 1. Clinician programmer 22 and patient programmer 24 may, for example, communicate via wireless communication with IMD 16 using RF telemetry techniques known in the art. Clinician programmer 22 and patient programmer 24 also may communicate with each other using any of a variety of local wireless communication techniques, such as RF communication according to the 802.11 or Bluetooth specification sets, infrared communication, e.g., according to the IrDA standard, or other standard or proprietary communication protocols.

An IMD 16 and/or programmer 22 may additionally or alternatively send information to a clinician, clinic and/or manufacturer of one or more components of system regarding one or more elements of systems 10 with integrity issues and, in some cases, actions automatically taken by an IMD 16 in response to the identification of the integrity issue. For example, programmer 22 may communicate with a clinician, clinician programmer 22, other computing device or system associated with a clinic and/or a computing device or system manufacturer via wireless communication, the Internet, a cellular network, or other standard or proprietary communication protocols. Two-way communication may be permitted to allow the clinician, clinic and/or manufacturer to send information or instructions for addressing an identified integrity issue to programmer 22 and/or an IMD 16. By allowing an IMD 16 and/or programmer 22 to communicate with a clinician, clinic and/or manufacturer, the need for patient 12 to visit the clinician may be eliminated. In some embodiments, IMD 16 may send data (e.g., anonymized data) to a system or database maintained by the manufacturer to, for example, aid the manufacturer in tracking system element reliability and/or therapy outcome trends.

Figure 2:
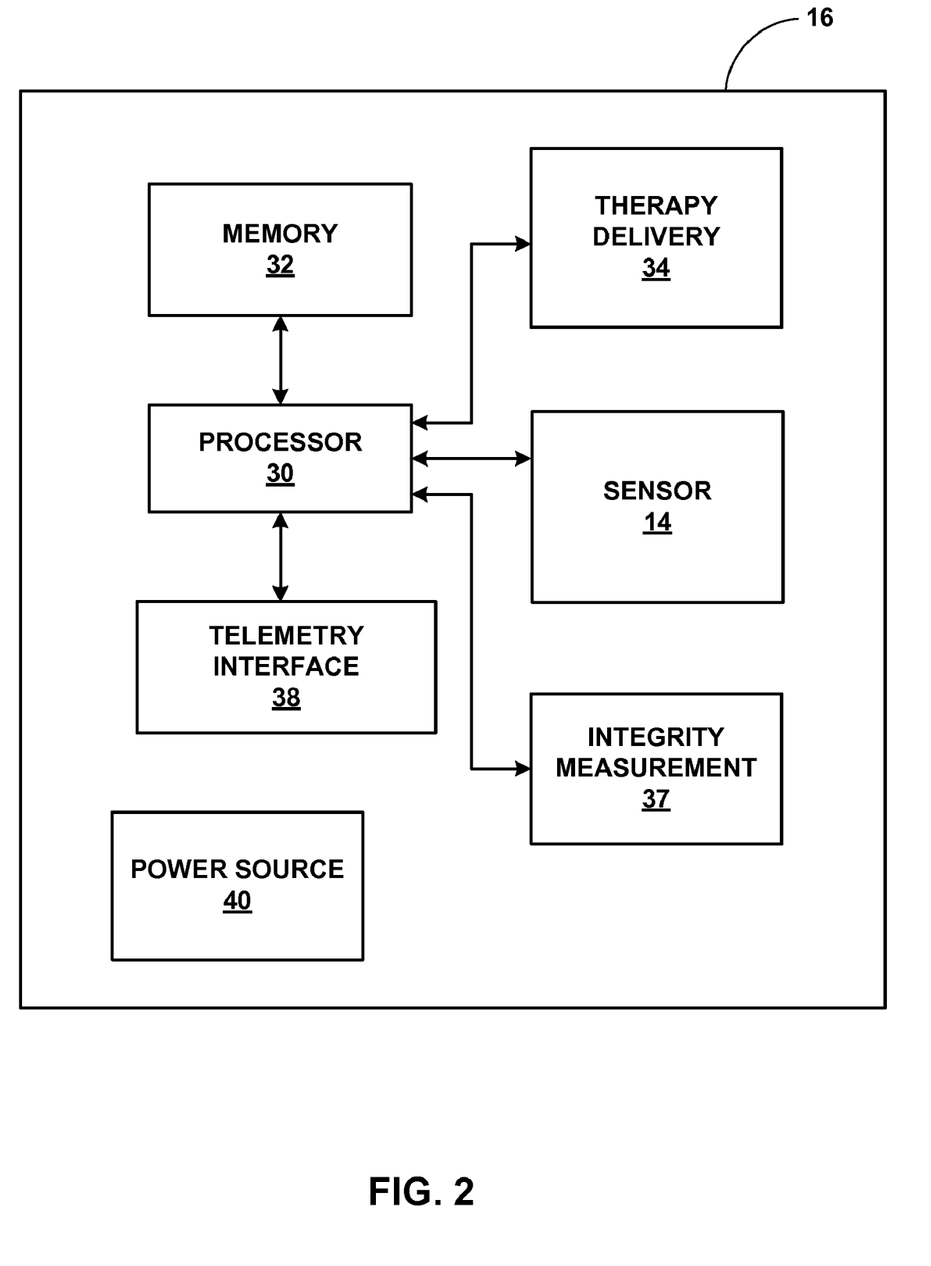
FIG. 2 is a functional block diagram illustrating an example implantable medical device that that performs automatic integrity tests.

FIG. 2 is a functional block diagram further illustrating an IMD 16 according to one embodiment. In the illustrated example, IMD 16 includes a processor 30, memory 32, therapy delivery module 34, sensor 14, integrity measurement module 37, a telemetry interface 38, and a power source 40. As illustrated by FIG. 2, IMD 16 may include one or more sensors 14 on or within a housing, as well as being coupled to sensors as illustrated in FIG. 1B.

Processor 30 is coupled to sensors 14, and may receive signals generated by sensors 14 as a function of one or more physiological parameters of patient 12. IMD 16 may include amplifiers, filters, analog-to-digital converters, or other circuitry (not shown) that conditions the signals for processing by processor 30. Processor 30 monitors the signals and may control therapy delivery module 34 to deliver therapy to patient 12 based on the signals. Therapy delivery module 34 may comprise an electrical signal generator, e.g., pulse generator, or a pump. Therapy delivery module 34 may be coupled to leads 21 (via extensions 19) or catheters 18, as examples.

Processor 30 also determines whether an event is detected, as described in further detail with respect to FIGS. 1A and 1B, and controls integrity measurement module 37 to automatically make an integrity measurement based on the determination. Integrity measurement module 37 may include resistors, capacitors, or other known circuitry for sampling and/or holding a value of a signal for analysis.

Memory 32 may store one or more sensing programs used to detect events, as well as one or more integrity measurement programs. In some embodiments, an integrity measurement program may include a sophisticated diagnostic program that may be executed by processor 30 using integrity measurement circuitry 37. For example, a sophisticated diagnostic program may call for a first, basic integrity measurement. Then, based on the outcome of the basic integrity measurement, the sophisticated diagnostic program may call for a second, diagnostic integrity measurement. For example, the basic integrity measurement may determine if therapy delivery system 10 is functioning properly, and the second, diagnostic integrity measurement may aid to determining why therapy delivery system 10 is not functioning properly if the basic integrity measurement detected a problem. The sophisticated diagnostic program may also include instructions to modify the therapy delivered by therapy delivery module 34 or send an alert to patient 12, a clinician, a clinic, or a manufacturer, as examples, based on the outcome of the integrity measurements.

In some embodiments, processor 30 may control therapy delivery module 34 to modify therapy delivery to patient 12 based on the integrity measurement. For example, if the integrity measurement detects a symptomatic event, processor 30 may control therapy delivery module 34 to deliver therapy to patient 12. Processor 30 may control telemetry interface 38 to deliver an alert to patient 12 (e.g., via patient programmer 24), clinician (e.g., via clinician programmer 22 and, in some cases, a network), or a remote clinic or manufacturer via a network, based on the integrity measurement. For example, if the integrity measurement detects a problem with the pump of therapeutic delivery device 16 that is prohibiting therapy delivery to patient 12, processor 30 may control telemetry interface 38 to alert patient 12 to take oral medications and/or see a clinician via patient programmer 22.

Processor 30 may include any one or more of a microprocessor, a controller, a digital signal processor (DSP), an application specific integrated circuit (ASIC), a field-programmable gate array (FPGA), discrete logic circuitry, or the like. Memory 32 may include for example any volatile, non-volatile, magnetic, optical, or electrical media. For example, memory 32 may include any one or more of a random access memory (RAM), read-only memory (ROM), non-volatile RAM (NVRAM), electronically erasable programmable ROM (EEPROM), flash memory, or the like.

Figure 3:
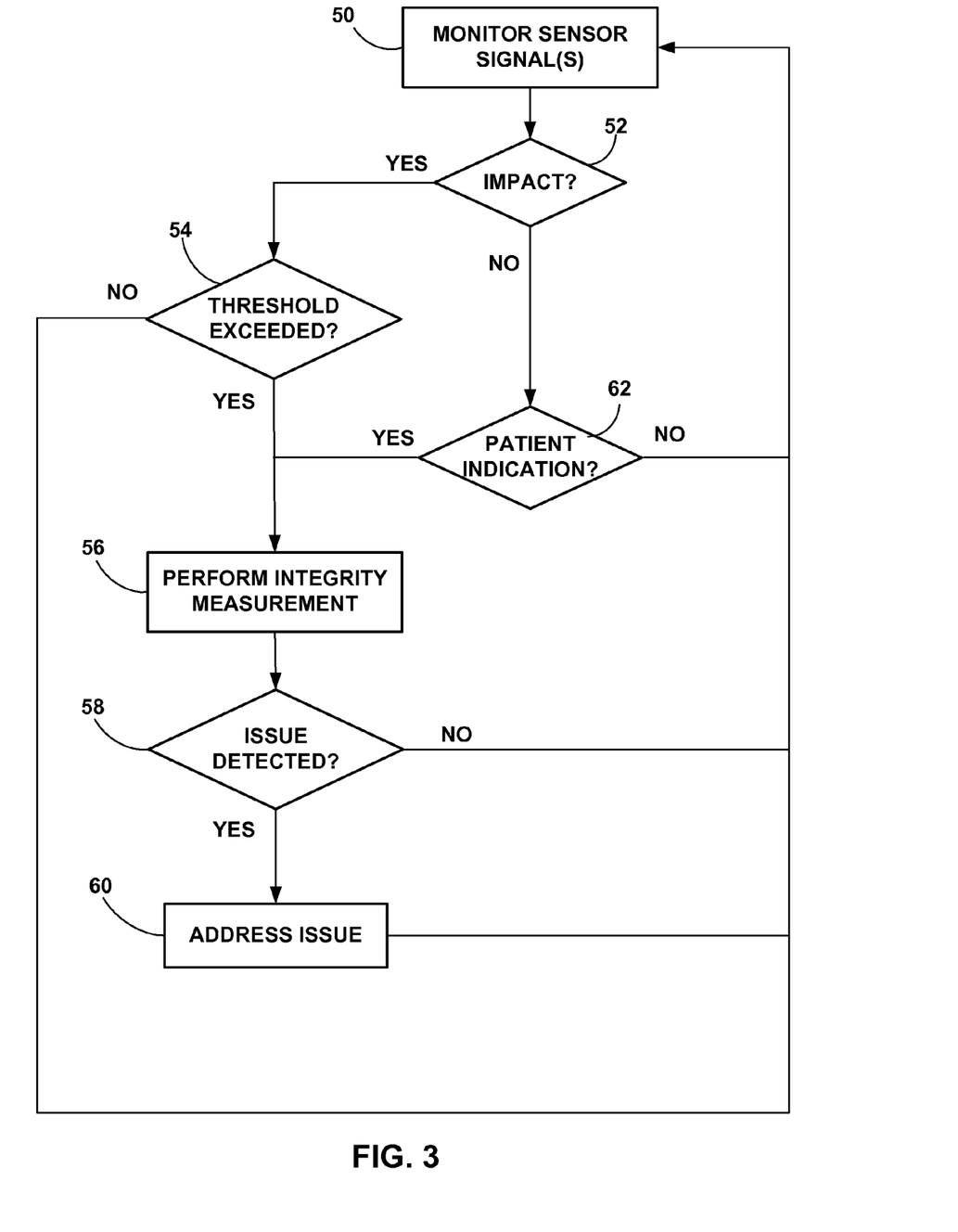
FIG. 3 is a flow diagram illustrating an example method for performing an integrity test based on a determination as to whether an event has been detected.

FIG. 3 is a flow diagram illustrating an example method of testing the integrity of at least one of a therapy delivery element, e.g., a lead or catheter, a sensor, a software element, a firmware element, or a hardware element based on a determination as to whether an external force exceeding a threshold, e.g., a system damage threshold, has been detected. According to the example method, IMD 16 and, more particularly, processor 30 of IMD 16, monitors a signal received from a sensor, e.g., one or more of sensing devices 14 or a sensor within IMD 16 (50). The sensor 14 may be a sensor that senses one or more of activity, posture, or pressure, such as an accelerometer, piezoelectric sensor, or pressure sensitive capacitor. Based on the signal, processor 30 determines whether a force, e.g., an impact, as illustrated in the example of FIG. 3, is detected (52). The force may cause an abrupt change in the signal from the sensor. Processor 30 determines if the force exceeds a threshold, e.g., a threshold associated with possible system damage, which may be predetermined and stored in memory 32 (54).

If the force exceeds the threshold, processor 30 controls integrity measurement module 37 to check the integrity of one or more of a therapy delivery element, a sensor, a software element, a firmware element, or a hardware element (56). For example, processor 30 may control integrity measurement module 37 to run software, hardware, and/or firmware diagnostics. As another example, processor 30 may control integrity measurement module 37 to test if a therapy delivery element (e.g., one or more of catheters 18) is functioning properly (e.g., by measuring a pressure within the therapy delivery element).

Based on the integrity measurement, processor 30 determines whether an issue is detected (58). For example, in the embodiment in which the integrity measurement comprises running hardware diagnostics, processor 30 may determine that an issue is detected based on the results of the hardware diagnostic test.

If processor 30 identifies an issue, processor 30 may address the issue (60) in any of the manners discussed herein. For example, processor 30 may provide an alert or message to a user, such as patient 12 or a clinician, via patient programmer 24, clinician programmer 22, and/or remotely via a network, as described above. Processor may additionally or alternatively provide an alert or message to a remote clinic or manufacturer via a network.

As a further example, if the integrity measurement takes the form of an impedance measurement and detects a dysfunctional electrical path based on the measured impedance, IMD 16 may modify a stimulation or sensing program to not use the dysfunctional electrical path and/or change other parameters, such as sensing gain or stimulation amplitude, to compensate for the dysfunctional path. Processor 30 may also attempt to fix the issue. For example, if the integrity measurement indicated that the pressure within a catheter 18 is high, suggestive of a possible occlusion within the catheter, processor 30 may control therapy delivery module 34 to increase the pump stroke in an attempt to clear the occlusion.

In some cases, a dysfunctional electrical path of a lead and/or an occlusion of a therapeutic substance delivery element may be intermittent. For example, an occlusion or short may only occur when patient 12 is in a particular position. For an intermittent issue, processor 30 may monitor the duration of the issue and/or identify a patient activity, position, or posture that corresponds with the intermittent dysfunction.

After the issue is no longer observed, processor 30 may control therapy delivery module to adjust therapy to attempt to make up for the therapy that was missed when the issue occurred. As one example, processor 30 may control a pump (e.g., of IMD 16B) to increase flow rate within safety bounds for a period of time such that the average dose (e.g., hourly or daily) equals the intended average dose that would have been delivered to patient 12B had the issue not occurred. Processor 30 may calculate the therapy missed and adjust subsequent therapy to make up for the missed therapy in a safe manner (e.g., without causing overdose or other side effects).

As another example, a stimulator (e.g., IMD 16A) delivering cycled or periodic stimulation may delay a stimulation period until the intermittent issue is no longer observed, e.g., until patient 12A changes posture and the lead (e.g. lead 21A or 21B) is no longer shorting. Additionally, as described above, processor 30 may advise patient 12, e.g., via patient programmer 24, to avoid the position, posture, or activity associated with the dysfunction until the problem can be resolved, e.g., until the patient visits a clinic.

If processor 30 does not identify an issue (58), processor 30 continues to monitor signals from one or more sensors (50). Further, processor 30 may determine whether an indication that a substantial impact (e.g., a fall or collision) occurred has been received from patient 12 (62). Failure to detect a reported impact based on the monitored signals from sensors 14 may also be indicative of a problem with therapy delivery system 10. Processor may receive the indication from patient 12, via patient programmer 24, by detecting "tapping" proximate to the implant site of IMD 16 via an accelerometer or piezoelectric element or accelerometer, by detecting placement of a magnet proximate to IMD 16, or any other suitable means. Processor 30 may control integrity measurements and address issues (56-60) as described above, in response to identifying a failed detection (62). In some embodiments, processor 30 may require one or more such indicated failures prior to performing an integrity measurement, e.g., to reduce energy and memory consumption. Frequent measurements consume energy, e.g., deplete an IMD battery, and may result in too great of an amount of measurement related data stored in memory 32.

Figure 4:
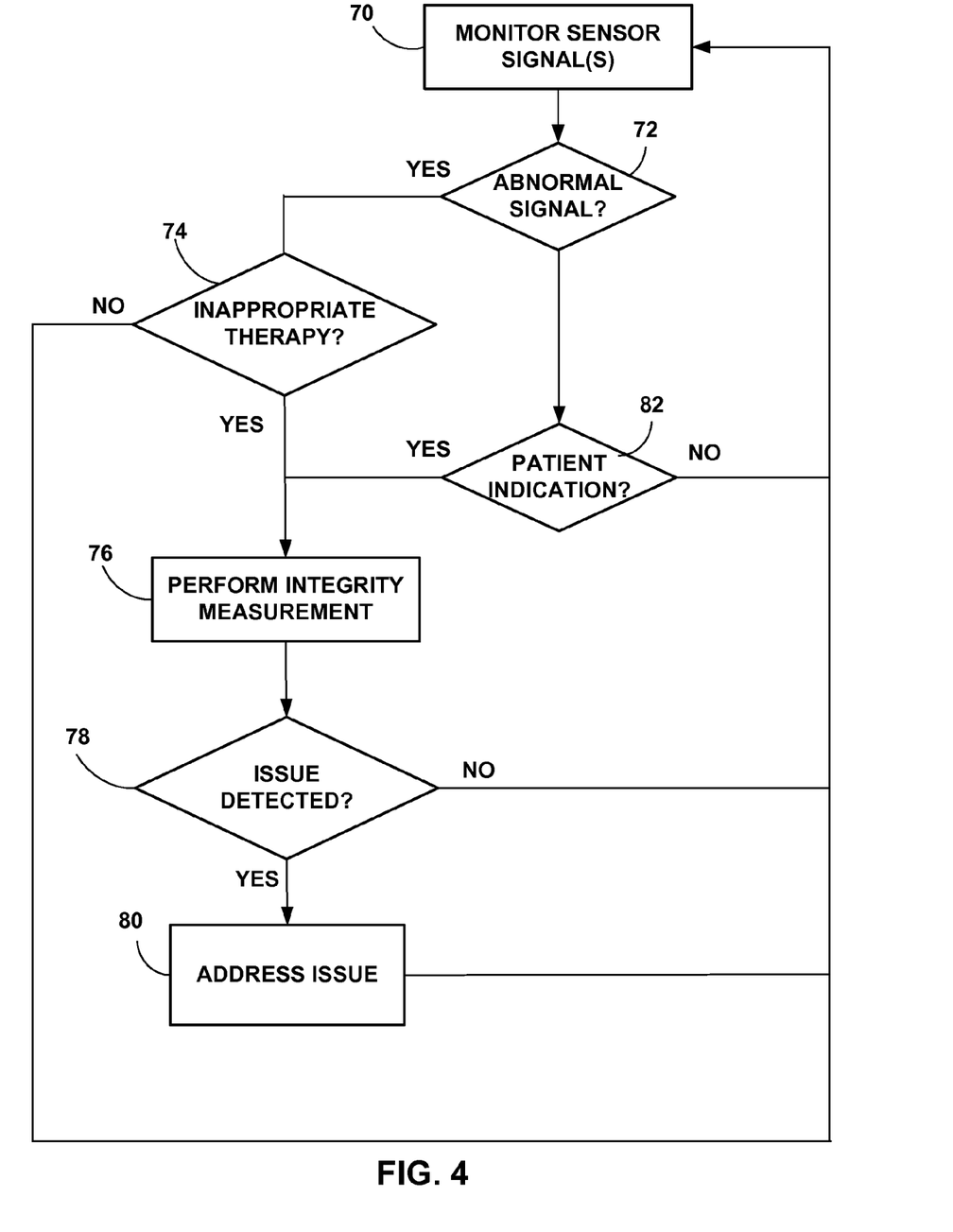
FIG. 4 is another flow diagram illustrating an example method for performing an integrity test based on a determination as to whether an event has been detected.

FIG. 4 is a flow diagram illustrating an example method of testing the integrity of at least one of a therapy delivery element, a sensor, a software element, a firmware element, or a hardware element based on a determination that patient 12 is not receiving adequate therapy based on a signal from a sensor that detects at least one of an activity or physiological state of a patient. According to the example method, IMD 16 and, more particularly, processor 30 of IMD 16, monitors a signal received from a sensor 14 (70). Based on the signal, processor 30 determines whether the sensed signal is abnormal (72). For example, an abnormal signal may include a quiescent (e.g., substantially flat) signal segment, contain abnormal energy content in a particular frequency band, be out of an expected physiological range, be saturated (e.g., out of a range detectable by the sensor), or exceed the allowable slew rate (e.g., demonstrate signal railing).

If an abnormal signal is detected, processor 30 determines if the therapy delivered to patient 12 is inadequate (74). For example, IMD 16 may test the sensor that is producing the abnormal signal to determine if the abnormal reading is due to patient 12 not receiving adequate therapy rather than a dysfunctional sensor. As another example, IMD 16 may analyze the signals from multiple sensors to determine if the abnormal reading is the result of a dysfunctional sensor or inadequate therapy delivery. If patient 12 is not receiving adequate therapy, it may be reflected in more than one sensor.

If IMD 16 determines that patient 12 is not receiving adequate therapy, processor 30 controls integrity measurement module 37 to check the integrity of a therapy delivery element, another sensor, e.g., a sensor other than the sensor with the abnormal signal that detects a different physiological parameter, a software element, a firmware element, or a hardware element (76). For example, processor 30 may control integrity measurement circuitry 37 to run software, hardware, and/or firmware diagnostics. As another example, processor 30 may control integrity measurement circuitry 37 to test if a therapy delivery element, e.g., one or more of catheters 18 or leads 21, is functioning properly, e.g., by measuring a pressure within the catheter or an impedance of one or more electrical paths within the lead.

Based on the integrity measurement, processor 30 determines whether an issue is detected (78). If processor 30 identifies an issue, processor 30 may address the issue as discussed above (80). If processor 30 does not identify an issue (78), processor 30 continues to monitor signals from one or more sensors (70).

Further, processor 30 may determine whether an indication that patient 12 is not receiving adequate therapy has been received from patient 12 (82). Inadequate therapy delivery may be indicative of a problem with therapy delivery system 10. Processor may receive the indication from patient 12, via patient programmer 24, by detecting "tapping" proximate to the implant site of IMD 16 via an accelerometer or piezoelectric element, by detecting placement of a magnet proximate to IMD 16, or any other suitable means. Processor 30 may control integrity measurements and address issues (76-80) as described above, in response to identifying an indication from patient 12 (82). In some embodiments, processor 30 may require one or more such indications prior to performing an integrity measurement, e.g., to reduce energy and memory consumption.

Figure 5:
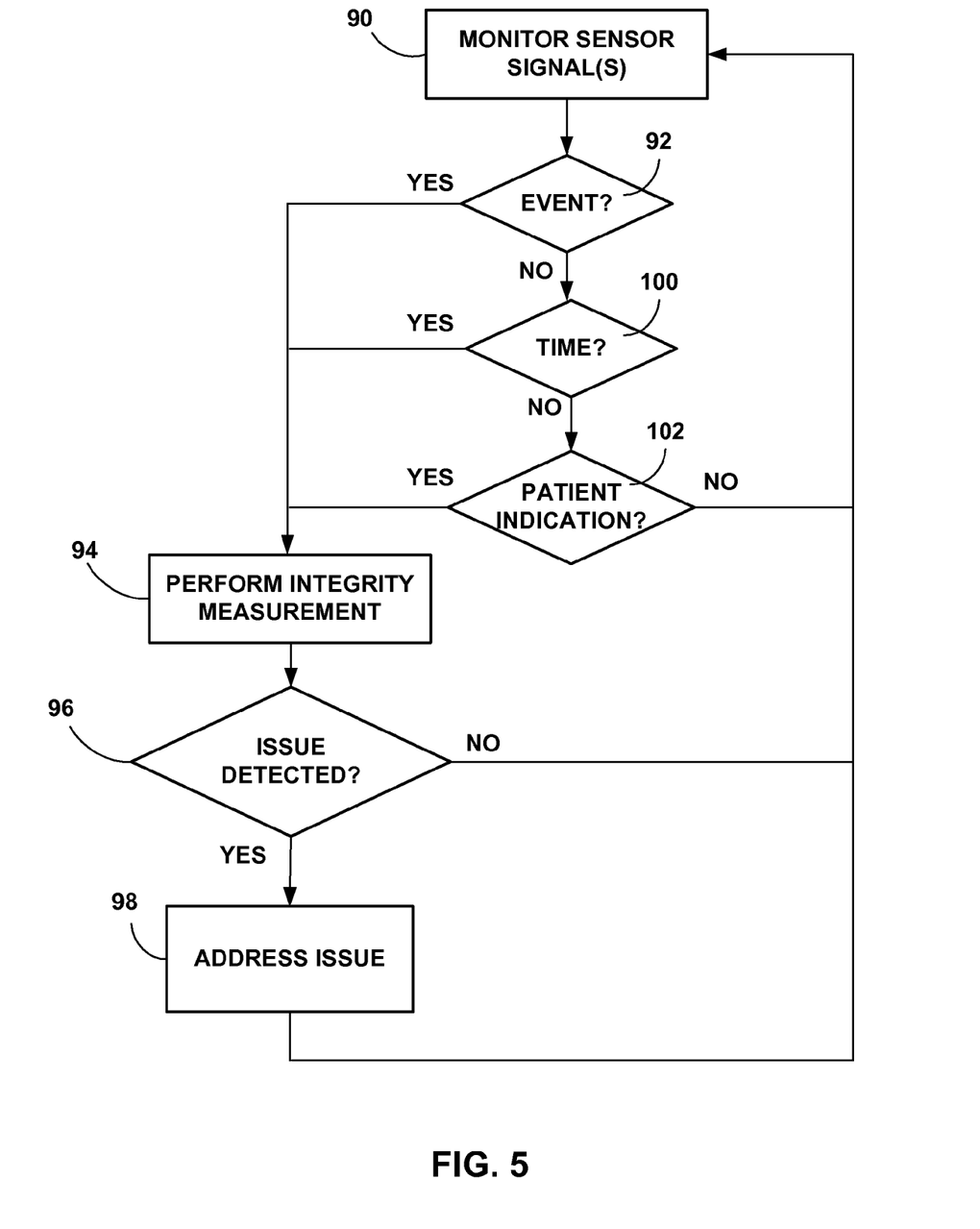
FIG. 5 is another flow diagram illustrating an example method for performing an integrity test based on a determination as to whether an event has been detected.

FIG. 5 is a flow diagram illustrating an example method of testing the integrity of a therapeutic substance delivery element, e.g., one or more of catheters 18 that deliver a therapeutic agent to patient 12, based on a determination as to whether an event has been detected. According to the example method, IMD 16 and, more particularly, processor 30 of IMD 16, monitors a signal received from one or more sensors 14 (90). Based on the signal, processor 30 determines whether an event, such as a symptomatic event, is detected (92). If the event is a symptomatic event, processor 30 may control therapy delivery module 34 to deliver therapy to patient 12.

Processor 30 controls integrity measurement module 37 to perform an integrity measurement in response to detection of an event (94). Processor 30 may control integrity measurement module 37 to automatically check integrity of a therapeutic substance delivery element in response to detection of an event.

Processor 30 may control circuitry 37 to perform integrity measurements after every detected event, or after every $N^{th}$ detected event, where N is an integer greater than 1. Measuring more frequently may allow IMD 16 or other devices, such as patient programmer 24 or clinician programmer 22, to more accurately identify when therapy delivery system 10 is not functioning properly. Whether or not integrity measurements are performed in response to each detected event may be determined based on the type of event detected. For example, if the detected event is an impact that exceeds a system damage threshold, it may be beneficial to perform an integrity measurement each time an event of this type is detected. However, if a detected event is a target activity state corresponding to a specific posture of patient 12, performing an integrity measurement after every detection of this type of event may not be necessary. Frequent measurements consume energy, e.g., deplete an IMD battery, and may result in too great of an amount of measurement related data stored in memory 32.

Based on the integrity measurement, processor 30 determines whether an issue is detected (96). For example, in embodiments in which the integrity measurement comprises measuring a pressure within a catheter, processor 30 may determine that an issue is detected by comparing the measured pressure to the normal pressure expected based on the flow rate of the therapeutic agent. Memory 32 may store a look up table with the expected pressure values and appropriate deviations to aid in the comparison. In particular, if the pressure value is above or below an expected pressure value stored in memory 32, processor 30 may determine that there is an issue with the catheter.

If processor 30 identifies an issue, processor 30 may address the issue (98). For example, if the integrity measurement indicated that the pressure within catheter 18 is low, suggestive of a possible tear in catheter 18 that is prohibiting the therapeutic agent from reaching its target delivery site, processor 30 may reduce or stop infusion until the issue is addressed. Processor 30 may also attempt to fix the issue. For example, if the integrity measurement indicated that the pressure within a catheter 18 is high, suggestive of a possible occlusion within the catheter 18, processor 30 may increase the pump stroke in an attempt to clear the occlusion. If processor 30 does not identify an issue (96), processor 30 continues to monitor signals for sensors 14 (90).

When processor 30 has not detected an event (92), processor 30 may further determine whether a threshold time period has passed since the last detection of an event (100). The time threshold may vary based on the type of event and may be used with certain types of events but not others. For example, if the detected event is a target activity state that occurs relatively frequently, the threshold time period may be used to help ensure that an integrity measurement is taken if the target activity state is not detected for a substantial time period. Lack of detection of the target activity state for the threshold time period may indicate that there is a problem with therapy delivery system 10. The detected event may be a posture change, a particular activity (e.g., walking), an EEG change, or an ECG change. Processor 30 may expect to detect each of these events periodically. A lack of such detections may indicate problems with the sensors used in the detections and/or severe problems with the patient. In contrast, if the detected event is an impact that exceeds a system damage threshold, a threshold time period may not be used. Since an impact that exceeds a system damage threshold may occur infrequently, it may not be necessary to make an integrity measurement if this type of event is not detected for a threshold time period.

Further, processor 30 may determine whether an indication that an event occurred has been received from patient 12 (102). Failure to detect a reported event based on the monitored signals from sensors 14 may also be indicative of a problem with therapy delivery system 10. Processor may receive the indication from patient 12, via patient programmer 24, by detecting "tapping" proximate to the implant site of IMD 16 via an accelerometer or piezoelectric element, by detecting placement of a magnet proximate to IMD 16, or any other suitable means. Processor 30 may control integrity measurements and address issues with therapy delivery system 10 (94-98) as described above, in response to identifying a time period without detection (100), or a failed detection (102). In some embodiments, processor 30 may require one or more such indicated failures prior to performing an integrity measurement, e.g., to reduce energy and memory consumption as previously described.

Various embodiments of the invention have been described. These and other embodiments are within the scope of the following claims.

The invention claimed is:

1. A method comprising:
  monitoring a signal from a sensor that detects a physiological parameter of a patient;
  determining whether an event is detected based on the signal; and
  automatically testing integrity of a therapeutic substance delivery element with another sensor based on the determination of whether the event is detected,
  wherein automatically testing integrity of the therapeutic substance delivery element with another sensor comprises at least one of measuring a pressure within the therapeutic substance delivery element, or measuring a flow of a therapeutic substance within the therapeutic substance delivery element, wherein the therapeutic substance delivery element delivers the therapeutic substance from an implantable medical device to a target therapy delivery site in the patient, and wherein the therapeutic substance delivery element comprises at least one of a pump within the implantable medical device or an implantable catheter coupled to the pump.

2. The method of claim 1, wherein determining whether an event is detected comprises at least one of determining whether the patient experienced a symptomatic event, or determining whether the patient is within a target activity state.

3. The method of claim 1, wherein the event comprises at least one of an abnormal signal from the sensor, or an external force with a magnitude that exceeds a threshold.

4. The method of claim 1, further comprising:
detecting an occlusion in the therapeutic substance delivery element based on the integrity test; and
altering a pumping characteristic of the pump within the medical device that delivers the therapeutic substance to the therapeutic substance delivery element to clear the occlusion.

5. The method of claim 1, further comprising providing an alert to the patient based on the integrity test.

6. The method of claim 1, wherein determining whether the event is detected comprises detecting the event, and wherein testing integrity comprises testing integrity in response to the detection.

7. The method of claim 1, wherein determining whether the event has been detected comprises determining that the event has not been detected for a threshold period of time, and testing integrity comprises testing integrity in response to the determination that the event has not been detected for the threshold period of time.

8. The method of claim 1, wherein determining whether the event has been detected comprises:
receiving an indication from the patient that the event occurred; and
determining that the event was not detected based on the signal from the sensor, and
wherein testing integrity comprises testing integrity in response to the determination that the event was not detected based on the signal from the sensor.

9. The method of claim 8, further comprising testing the integrity of the sensor in response to the determination that the event was not detected based on the signal from the sensor.

10. The method of claim 1, wherein determining whether the event is detected comprises detecting the event, wherein testing integrity comprises testing integrity every $N^{th}$ time the event is detected, and wherein N is an integer greater than 1.

11. The method of claim 1, further comprising:
detecting an intermittent occlusion in the therapeutic substance delivery element based on the integrity test;
monitoring a duration of the occlusion; and
adjusting delivery of the therapeutic substance to make up for therapy missed throughout the duration of the occlusion.

12. The method of claim 1, wherein the therapeutic substance comprises at least one of a pharmaceutical agent, insulin, a pain relieving agent, and a gene therapy agent.

13. An implantable medical device comprising:
an integrity measurement module configured to test integrity of a therapeutic substance delivery element that delivers a therapeutic substance from the implantable medical device to a target therapy delivery site in a patient; and a processor that monitors a signal from a sensor that detects a physiological parameter of the patient, determines whether an event is detected based on the signal, and automatically controls the integrity measurement module to test integrity of the therapeutic substance delivery element with another sensor based on the determination, wherein the processor controls the integrity measurement module to at least one of measure a pressure within the therapeutic substance delivery element, or measure flow of the therapeutic substance within the therapeutic substance delivery element to test the integrity of the therapeutic substance delivery element, wherein the therapeutic substance delivery element comprises at least one of a pump within the implantable medical device or an implantable catheter coupled to the pump.

14. The implantable medical device of claim 13, wherein the event comprises a symptomatic event experienced by the patient.

15. The implantable medical device of claim 13, wherein the event comprises the patient being within a target activity state.

16. The implantable medical device of claim 13, wherein the event comprises at least one of an abnormal signal from the sensor, or an external force with a magnitude that exceeds a threshold.

17. The implantable medical device of claim 13, further comprising a pump that delivers the therapeutic substance to the therapeutic substance delivery element, wherein the processor detects an occlusion in the therapeutic substance delivery element based on the integrity test, and alters a pumping characteristic of the pump to clear the occlusion.

18. The implantable medical device of claim 13, wherein the processor detects the event based on the signal, and controls the integrity measurement module to test integrity of the therapeutic substance delivery element in response to the detection.

19. The implantable medical device of claim 13, wherein the processor determines that the event has not been detected for a threshold period of time, and controls the integrity measurement module to test integrity of the therapeutic substance delivery element in response to the determination that the event has not been detected for the threshold period of time.

20. The implantable medical device of claim 13, wherein the processor receives an indication from the patient that the event occurred, determines that the event was not detected based on the signal from the sensor, and controls the integrity measurement module to test integrity of the therapeutic substance delivery element in response to the determination that the event was not detected based on the signal from the sensor.

21. The implantable medical device of claim 20, wherein the processor controls the integrity measurement module to test integrity of the sensor in response to the determination that the event was not detected based on the signal from the sensor.

22. The implantable medical device of claim 13, wherein the processor detects an intermittent occlusion in the therapeutic substance delivery element based on the integrity test, monitors a duration of the occlusion, and adjusts delivery of the therapeutic substance to make up for therapy missed throughout the duration of the occlusion.

23. The device of claim 13, wherein the therapeutic substance comprises at least one of a pharmaceutical agent, insulin, a pain relieving agent, and a gene therapy agent.

24. A method comprising:
monitoring a first signal from a first sensor of an implantable medical device system, wherein the first signal from the first sensor varies as a function of a first physiological parameter of a patient;
detecting an abnormality in the first monitored signal, wherein the abnormality includes values outside of an expected physiological range;
in response to detection of the abnormality, determining whether the first sensor is functioning properly based on the first monitored signal that includes the abnormality and based on signals from one or more additional sensors;
determining that the patient is not receiving appropriate therapy if the first sensor is determined to be functioning properly; and
automatically testing integrity of at least one other element of the implantable medical device system based on the determination that the patient is not receiving appropriate therapy,
wherein the at least one other element comprises at least one of a therapy delivery element, one of the one or more additional sensors, a software element, a firmware element, or a hardware element.

25. The method of claim 24, wherein the abnormality includes unexpected energy content in a particular frequency band.

26. The method of claim 24, further comprising providing an alert to the patient based on the integrity test.

27. The method of claim 24, wherein the therapy delivery element comprises at least one of a lead carrying at least one electrode that delivers electrical stimulation to the patient, or a therapeutic substance delivery element that delivers a therapeutic substance to a target therapy delivery site in the patient.

28. The method of claim 24, wherein each of the first sensor and additional sensors comprises at least one of an electrode, an accelerometer, a sensor that detects at least one of activity or posture, an electroencephalogram sensor, an electromyogram sensor, an electrocardiogram sensor, a chemical sensor, an optical sensor, a pressure sensor, or a temperature sensor.

29. An implantable medical device comprising:
an integrity measurement module; and
a processor configured to:
monitor, via a first sensor, a signal that varies as a function of a first physiological parameter of a patient;
detect an abnormality in the monitored signal, wherein the abnormality includes values outside of an expected physiological range;
in response to detection of the abnormality, determine whether the first sensor is functioning properly based on the monitored signal that includes the abnormality and based on signals from one or more additional sensors;
determine that a patient is not receiving adequate therapy if the first sensor is determined to be functioning properly; and
automatically control the integrity measurement module to test integrity of at least one other element of an implantable medical device system that includes the implantable medical device based on the determination that the patient is not receiving appropriate therapy,
wherein the at least one other element comprises at least one of a therapy delivery element, one of the one or more additional sensors, a software element, a firmware element, or a hardware element.

30. The implantable medical device of claim 29, wherein the abnormality includes unexpected energy content in a particular frequency band.

31. The implantable medical device of claim 29, wherein the processor provides an alert to the patient based on the integrity test.

32. A method comprising:
monitoring a signal from a sensor of an implantable medical device system that detects at least one of activity, posture, or pressure;
detecting, based on the signal, a force external to a patient, the force having a magnitude that exceeds a threshold associated with possible system damage; and
automatically testing integrity of at least one element of the implantable medical device system in response to the detection,
wherein the at least one element comprises at least one of a therapy delivery element, the sensor, another sensor that detects another physiological parameter of the patient, a software element, a firmware element, or a hardware element.

33. The method of claim 32, further comprising providing an alert to the patient based on the integrity test.

34. The method of claim 32, wherein the sensor comprises an accelerometer.

35. The method of claim 32, wherein the therapy delivery element comprises at least one of a lead carrying at least one electrode that delivers electrical stimulation to the patient, or a therapeutic substance delivery element that delivers a therapeutic substance to a target therapy delivery site in the patient.

36. The method of claim 32, wherein the at least one element comprises at least one of an electrode, an accelerometer, a sensor that detects at least one of activity or posture, an electroencephalogram sensor, an electromyogram sensor, an electrocardiogram sensor, a chemical sensor, an optical sensor, a pressure sensor, or a temperature sensor.

37. The method of claim 32, wherein the force comprises at least one of an acceleration or an external impact.

38. The method of claim 32, wherein the threshold is indicative of one of a fall or a collision.

39. An implantable medical device comprising:
an integrity measurement module; and
a processor configured to:
monitor a signal from a sensor that detects at least one of activity, posture, or pressure;
detect, based on the signal, a force external to a patient, the force having a magnitude that exceeds a threshold associated with possible system damage; and
automatically test integrity of at least one element of an implantable medical device system in response to the detection,
wherein the at least one element comprises at least one of a therapy delivery element, the sensor, another sensor that detects another physiological parameter of the patient, a software element, a firmware element, or a hardware element.

40. The medical device of claim 39, wherein the processor provides an alert to the patient based on the integrity test.

41. The medical device of claim 39, wherein the sensor comprises an accelerometer.

42. The medical device of claim 39, wherein the force comprises at least one of an acceleration or an external impact.

43. The implantable medical device of claim 39, wherein the threshold is indicative of one of a fall or a collision.

* * * * *